US 011110281B2

(12) United States Patent
Mi et al.

(10) Patent No.: US 11,110,281 B2
(45) Date of Patent: Sep. 7, 2021

(54) SECURE TRANSDERMAL COMMUNICATION WITH IMPLANTED DEVICE

(71) Applicant: Cardiac Pacemakers, Inc., St. Paul, MN (US)

(72) Inventors: Bin Mi, Arden Hills, MN (US); Jonathan Bennett Shute, Minnetonka, MN (US); Kenneth P. Hoyme, Plymouth, MN (US); Grace Ann Wiechman, Minneapolis, MN (US); Michael Sheehan Seeberger, Afton, MN (US); Andrew Bomett, Inver Grove Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 287 days.

(21) Appl. No.: 16/239,395

(22) Filed: Jan. 3, 2019

(65) Prior Publication Data

US 2019/0201702 A1 Jul. 4, 2019

Related U.S. Application Data

(60) Provisional application No. 62/613,678, filed on Jan. 4, 2018.

(51) Int. Cl.
*A61N 1/00* (2006.01)
*A61N 1/372* (2006.01)
(Continued)

(52) U.S. Cl.
CPC .......... *A61N 1/37254* (2017.08); *A61B 5/117* (2013.01); *A61B 5/686* (2013.01);
(Continued)

(58) Field of Classification Search
CPC ............ A61N 1/37254; A61N 1/37252; A61N 1/37217–37229; A61N 1/37282;
(Continued)

(56) References Cited

U.S. PATENT DOCUMENTS 5,935,078 A 8/1999 Feierbach
6,223,018 B1 4/2001 Fukumoto et al.
(Continued)

FOREIGN PATENT DOCUMENTS

EP 2438959 4/2012
WO 2016133813 8/2016
(Continued)

OTHER PUBLICATIONS

Ferguson, John E. et al., "Wireless communication with implanted medical devices using the conductive properties of the body," Expert Rev Med Devices. Jul. 2011; 8(4): 427-433 (14 pages).
(Continued)

*Primary Examiner* — Scott M. Getzow
(74) *Attorney, Agent, or Firm* — Pauly, DeVries Smith & Deffner LLC

(57) ABSTRACT

A system and method for communication between an IMD and an external reader includes bringing a portion of a patient's body into contact with a device-body contact surface of an external reader. The reader transmits a first transdermal carrier wave from the contact surface into the patient's body, where the first carrier wave includes a request for communication with the IMD. The transdermal carrier waves are electrical conductive waves, optical waves, or acoustic waves. Upon detection of the first carrier wave, the IMD transmits a second transdermal carrier wave including a request for an access key from the reader and the reader replies by transmitting a third transdermal carrier wave including the access key back to the IMD. If the access key
(Continued)

is valid, the IMD transmits information by radio frequency (RF) in an RF communication mode or a fourth transdermal carrier wave including data from the IMD.

20 Claims, 7 Drawing Sheets

(51) Int. Cl.
| | |
|---|---|
| A61B 5/00 | (2006.01) |
| H04W 12/04 | (2021.01) |
| H04L 29/06 | (2006.01) |
| H04W 12/06 | (2021.01) |
| H04W 4/80 | (2018.01) |
| A61M 5/142 | (2006.01) |
| A61M 5/172 | (2006.01) |
| A61B 5/117 | (2016.01) |
| A61B 5/145 | (2006.01) |

(52) U.S. Cl.
CPC ...... *A61M 5/14276* (2013.01); *A61M 5/1723* (2013.01); *A61N 1/37217* (2013.01); *A61N 1/37282* (2013.01); *H04L 63/0492* (2013.01); *H04L 63/061* (2013.01); *H04L 63/0861* (2013.01); *H04W 4/80* (2018.02); *H04W 12/04* (2013.01); *H04W 12/06* (2013.01); *A61B 5/14532* (2013.01); *A61M 5/14248* (2013.01); *A61M 2205/502* (2013.01); *A61N 1/37235* (2013.01)

(58) Field of Classification Search
CPC .. A61N 1/37235; H04W 12/04; H04W 12/06; H04W 4/80; H04L 63/0861; H04L 63/061; A61M 5/14276; A61M 5/1723; A61M 2205/502; A61M 5/14248; A61B 5/117; A61B 5/686; A61B 5/14532
See application file for complete search history.

(56) References Cited

U.S. PATENT DOCUMENTS

| | | | |
|---|---|---|---|
| 6,277,078 B1 | 8/2001 | Porat et al. | |
| 6,336,903 B1 | 1/2002 | Bardy | |
| 6,368,284 B1 | 4/2002 | Bardy | |
| 6,398,728 B1 | 6/2002 | Bardy | |
| 6,411,840 B1 | 6/2002 | Bardy | |
| 6,440,066 B1 | 8/2002 | Bardy | |
| 6,764,446 B2 | 7/2004 | Wolinsky et al. | |
| 7,425,200 B2 | 9/2008 | Brockway et al. | |
| 10,682,517 B2 | 6/2020 | Hoffman et al. | |
| 2002/0077673 A1 | 6/2002 | Penner et al. | |
| 2002/0082480 A1 | 6/2002 | Riff et al. | |
| 2002/0177782 A1 | 11/2002 | Penner | |
| 2005/0021370 A1 | 1/2005 | Riff et al. | |
| 2009/0048644 A1 | 2/2009 | Stahmann et al. | |
| 2014/0273824 A1* | 9/2014 | Fenner | H04W 12/003 455/41.1 |
| 2016/0213937 A1* | 7/2016 | Reinke | A61N 1/3756 |
| 2018/0146374 A1* | 5/2018 | Golan | G06Q 20/127 |
| 2019/0083039 A1 | 3/2019 | Shute et al. | |
| 2019/0083041 A1 | 3/2019 | Shute et al. | |
| 2020/0364327 A1 | 11/2020 | Shute et al. | |

FOREIGN PATENT DOCUMENTS

| | | |
|---|---|---|
| WO | 2017189187 | 11/2017 |
| WO | 2019136233 | 7/2019 |

OTHER PUBLICATIONS

Challa, Sravani et al., "Authenitcation Protocols for Implantable Medical Devices: Taxonomy, Analysis and Future Directions," IEEE Consumer Electronics Magazine vol. 7, No. 1, Jan. 1, 2018 pp. 57-65 (9 pages).

"International Search Report and Written Opinion," for PCT Application No. PCT/US2019/012328 dated Apr. 16, 2019 (14 pages).

Marin, Eduard et al., "A Survey on Physiological-signal-based security for medical devices," International Association for Cryptologic Research vol. 20160910:154345, Sep. 6, 2016 pp. 1-16 (16 pages).

Rushanan, Michael et al., "SoK: Security and Privacy in Implantable Medical Devices and Body Area Networks," 2014 IEEE Symposium on Security and Privacy (16 pages).

Heather, Kenedi et al., "A Novel Authentication Biometric for Pacemakers," Presentation, 2018 IEEE/ACM International Conference on Connected Health: Applications, Systems and Engineering Tehnologies (CHASE), Sep. 26-28, 2018, Washington, DC, USA (7 pages).

"International Preliminary Report on Patentability," for PCT Application No. PCT/US2019/012328 dated Jul. 16, 2020 (10 pages).

\* cited by examiner

SECURE TRANSDERMAL COMMUNICATION WITH IMPLANTED DEVICE

This application claims the benefit of U.S. Provisional Application No. 62/613,678, filed Jan. 4, 2018, the content of which is herein incorporated by reference in its entirety.

BACKGROUND

Many implanted medical devices (IMDs) have significant onboard data storage capabilities. Sensitive patient data is included on the onboard data of many IMDs, as well as valuable and useful patient data. Security of the data on IMDs is a high priority. The ability to appropriately access the onboard data of an IMD is a competing high priority, especially in the context of emergency patient care.

SUMMARY

One general aspect includes bringing a portion of a patient's body into contact with a device-body contact surface of an external reader, where an IMD is implanted in the patient. The aspect also includes the reader transmitting a first transdermal carrier wave from the contact surface into the patient's body, where the first carrier wave includes a request for communication with the IMD. The aspect also includes, upon detection of the first carrier wave, the IMD transmitting a second transdermal carrier wave including a request for an access key from the reader. The aspect also includes, upon detection of the second transdermal carrier wave, the reader transmitting a third transdermal carrier wave including the access key back to the IMD. The aspect also includes the IMD examining the access key for validity. If the access key is valid, the IMD transmits one of the group of information by radio frequency (RF) in an RF communication mode and a fourth transdermal carrier wave including data from the IMD. Other embodiments of this aspect include corresponding computer systems, apparatus, and computer programs recorded on one or more computer storage devices, each configured to perform the actions of the methods.

Implementations may include one or more of the following features. If the access key is valid, the IMD provides power to an RF transceiver of the IMD. If the access key is valid, the IMD transmits by RF one of the group including of: data from the IMD, and an RF key needed for further communication with the IMD. The first, second, third and fourth transdermal carrier waves are selected from the group including electrical conductive waves, optical waves and acoustic waves. The second transdermal carrier wave sent from the IMD includes an IMD value present in a specific memory location of the IMD, and the access key sent by the reader in the third transdermal carrier wave is based on the IMD value present in the specific memory location of the IMD. The second transdermal carrier wave sent from the IMD includes a first request related to a medical record that is stored on the IMD, and the access key sent by the reader in the third transdermal carrier wave is based on the medical record. The first request related to the medical record is one of the group of: a waveform request for a physiological waveform of the patient from a specified time period that exists in storage on the IMD, an EGM request for an electrocardiogram waveform of the patient from a specified time period that exists in storage on the IMD, a sample request for sparsely-sampled, noncontiguous medical data that exists in storage on the IMD, an episode report request for a portion of an episode report that exists in storage on the IMD, and a calculation request for a calculation using as input values of medical record data in storage on the IMD. Bringing a portion of a patient's body into contact includes bringing a fingerprint of a patient into contact with the device-body contact surface, further including: the reader reading a fingerprint of the patient using the device-body contact surface, and the reader generating the access key based on the fingerprint of the patient. The IMD uses energy from the first transdermal carrier wave to power the transmission of the second transdermal carrier wave. The first carrier wave includes a request for a patient safety communication and a patient-safety access key, where patient-safety communication includes one of the group including of the patient's name, the patient's allergies, the patient's blood type and the patient's emergency contact information. Implementations of the described techniques may include hardware, a method or process, or computer software on a computer-accessible medium.

One general aspect includes a system for communication between an implanted medical device (IMD) implanted in a patient and an external reader. The IMD capable of being implanted into a patient's body includes a transdermal wave transceiver and a radio frequency transceiver. The external reader includes a device-body contact surface, a transdermal wave transceiver capable of transmitting transdermal carrier waves from the contact surface into the patient's body, and a radio frequency transceiver. The reader is operable to transmit a first transdermal carrier wave from the contact surface into the patient's body, where the first carrier wave includes a request for communication with the IMD. Upon detection of the first carrier wave, the IMD is operable to transmit a second transdermal carrier wave including a request for an access key code from the reader. Upon detection of the second transdermal carrier wave, the reader is operable to transmit a third transdermal carrier wave including the access key back to the IMD. The IMD is operable to examine the access key for validity upon receipt from the reader. If the access key is valid, the IMD is operable to transmit one of the group of: information by radio frequency (RF) in an RF communication mode and a fourth transdermal carrier wave including data from the IMD. Other embodiments of this aspect include corresponding computer systems, apparatus, and computer programs recorded on one or more computer storage devices, each configured to perform the actions of the methods.

Implementations may include one or more of the following features. The reader is configured to be in communication with a care server, where the care server includes stored medical records for the patient identical to medical records stored on the IMD. The IMD includes an energy harvesting circuit operable to use energy from the first transdermal carrier wave to power the transmission of the second transdermal carrier wave. Implementations of the described techniques may include hardware, a method or process, or computer software on a computer-accessible medium.

One general aspect includes a method of communication between an implanted medical device (IMD) implanted in a patient and an external reader, including: bringing a portion of a patient's body into contact with a device-body contact surface of an external reader, where an IMD is implanted in the patient; the reader transmitting a first transdermal electrical conductive wave from the contact surface into the patient's body, where the first transdermal electrical conductive wave includes a request for communication with the IMD; upon detection of the first transdermal electrical conductive wave, the IMD transmitting a second transdermal electrical conductive wave including a request for an access key from the reader; upon detection of the second transdermal electrical conductive wave, the reader transmitting a third transdermal electrical conductive wave including the access key back to the IMD; the IMD examining the access key for validity; if the access key is valid, the IMD providing power to a radio frequency (RF) transceiver of the IMD and transmitting IMD data in an RF communication mode. Other embodiments of this aspect include corresponding computer systems, apparatus, and computer programs recorded on one or more computer storage devices, each configured to perform the actions of the methods.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense.

Figure 1:
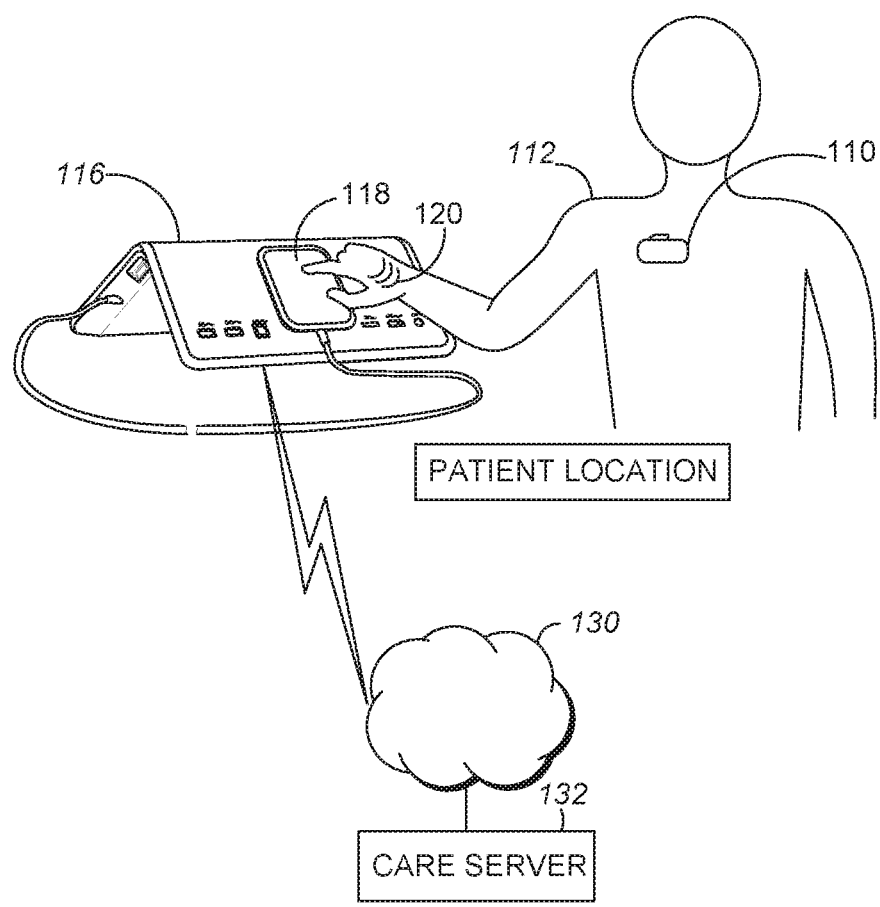
FIG. 1 is a schematic view of a communication system for communication between an implanted medical device (IMD) at a patient location and an external reader, where the system includes a care server, the patient is touching a body-contact surface of the reader, and transdermal carrier waves are moving through the patient's body from the reader to the IMD.

While embodiments herein are susceptible to various modifications and alternative forms, specifics thereof have been shown by way of example and drawings, and will be described in detail. It should be understood, however, that the scope herein is not limited to the particular examples described. On the contrary, the intention is to cover modifications, equivalents, and alternatives falling within the spirit and scope herein.

DETAILED DESCRIPTION

A method and a system for secure communication between an implanted medical device (IMD) in a patient's body and an external reader device are described herein. A transdermal communication mode is used to validate an access key in order to authorize transmission of data from the IMD. Once the access key is validated, IMD data can be transmitted using a radio-frequency (RF) communication mode between the IMD and the reader, or the IMD data can be provided using the transdermal communication mode.

A transdermal carrier wave is a wave that propagates through body tissue using physical contact with the body. One example of body contact is skin contact. Examples of transdermal carrier waves are electrical conductive waves, acoustic waves and optical waves. The reader includes a body-contact surface for facilitating contact between the reader and the patient's body. Both the IMD and the reader have a transdermal communication transceiver and an RF transceiver to facilitate the use of the transdermal communication mode and the RF communication mode.

In order to enable IMD data transmission to the reader, the reader provides an access key in the transdermal communication mode to unlock the RF communication mode or transdermal mode communication of IMD data. There are many different examples of how the access key can be determined or generated. In some examples, the access key exists within the IMD, such as at a stored memory location or within a medical record stored on the IMD. In some examples, the access key is derivable from information that exists within the IMD, such as at a stored memory location or within a medical record stored on the IMD. In some examples, the access key is derivable from data that is stored on the IMD and is also stored in the patient's medical record. In some examples, the access key is generated based on the patient's fingerprint or other biometric data.

In one example, the reader is in communication with a care server. The care server can store patient medical records, including medical records identical to the medical records stored on the IMD. In some example, the reader uses access to the medical records on the care server to produce the access key.

In one example of a method of communication between an IMD and a reader, a patient having an IMD brings a portion of the patient's body into contact with a device-body contact surface of the reader. The reader transmits a first transdermal carrier wave from the contact surface into the patient's body requesting communication with the IMD. Upon detection of the first carrier wave, the IMD replies with a second transdermal carrier wave requesting an access key from the reader. In some examples, the IMD can use energy from a detected transdermal carrier wave, such as the first transdermal carrier wave, to power the transmission of a subsequent transdermal carrier wave, such as the second transdermal carrier wave.

Upon detection of the second transdermal carrier wave, the reader transmits a third transdermal carrier wave comprising an access key back to the IMD. The IMD then examines the access key for validity. If the access key is valid, the IMD either transmits information by radio frequency (RF) in an RF communication mode, or sends data from the IMD using a fourth transdermal carrier wave.

In one example, the RF transceiver of the IMD is not powered on until the access key is validated by the IMD. Once the access key is provided by the reader using the transdermal communication mode and validated by the IMD, the RF transceiver of the IMD is powered on and RF communication begins between the IMD and the reader.

Figure 2:
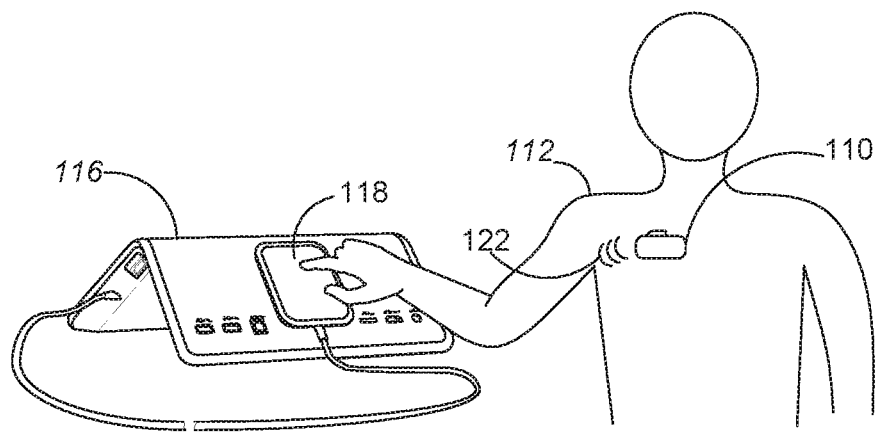
FIG. 2 is a schematic view of a patient with an implanted IMD and the external reader of FIG. 1, where transdermal carrier waves are moving through the patient's body from the IMD to the reader.

Secure Transdermal Communication System of FIGS. 1-2

FIG. 1 is a schematic view of an example communication system for communication between an implanted medical device (IMD) at a patient location and an external reader, where the system includes a care server, the patient is touching a body-contact surface of the reader, and transdermal carrier waves are moving through the patient's body from the reader to the IMD. An IMD 110 is implanted in the body of a patient 112. An external reader 116 is a device located outside of the patient's body that is capable of communicating with the IMD 110.

The reader 116 is capable of at least two different communication modes: a transdermal communication mode and a radio frequency (RF) communication mode. The reader 116 and the IMD 110 each have a transdermal wave transceiver and an RF transceiver. The transdermal communication mode is used to validate an access key in order to authorize transmission of IMD data from the IMD 110.

In FIG. 1, a transdermal carrier wave 120 is shown being transmitted from the reader 116 to the IMD 110. In FIG. 2, a transdermal carrier wave 122 is shown being transmitted from the IMD 110 to the reader 116.

The external reader 116 includes a device body contact surface 118. The device body contact surface 118 is provided to facilitate physical body contact between the reader 116 and the patient 112. FIG. 1 shows the patient 112 contacting the device body contact surface 118 with a fingertip, which is one example of device body contact to facilitate the transdermal communication mode. Other examples of device body contact are touching the device body contact surface 118 to any other part of the patient's skin, mouth or other body part.

In order to enable IMD data transmission to the reader 116, the reader 116 provides an access key in the transdermal communication mode to unlock communication of IMD data. The access key may be derivable from information in a medical record stored in the IMD 110 and also stored on a storage media. One example of a storage media for storing IMD data, medical records of patients with IMDs, and other data is a care server 132. It is also possible for the storage media to be a portable storage device, such as a flash drive or magnetic card. Although the term "server" will be used to describe the storage location in a number of embodiments described herein, it will be understood that it is also possible for the same data to be stored on a storage media different than a server. In one embodiment, the reader has a local memory location that includes IMD data and patient medical record data. In addition or alternatively, some information is stored in a local memory location while some is stored on an external storage media such as a server.

The reader 116 may have a communication link to the care server 132. The communication link between the reader 116 and the care server 132 may be via phone lines, a wired network, the Internet 130, a pervasive wireless network, or any other data connection. The reader 116 can also be used when it is not in communication with an IMD device, but is only in communication with the care server 132. In some examples, the reader 116 can also be used when it is not in communication with the care server 132, but is only in communication with an IMD.

Generally, a pervasive wireless communication network is a communications network that can be used to directly communicate with a host computer without the need for a repeater device. A pervasive network includes those networks that are sufficiently prevalent or dispersed that an average person in the U.S. would be within range of interfacing with the network at some point during a normal daily routine. A pervasive wireless network typically has a relatively broad effective geographic span. There are many different usable pervasive wireless communication networks. One example is a wireless telephone network, such as a cellular telephone network. Other example embodiments of a pervasive wireless communication network include a wireless pager network, wireless wide area networks (WAN), such as those installed in certain public places like coffee shops, airports, schools, or municipalities, and wireless local area networks (LAN) including those following the standards set forth by the Institute for Electrical and Electronic Engineers (IEEE) in Standards 802.11 (b) and (g).

The care server 132 may include many types of information that are regularly downloaded from the IMD, are input in other ways about the patient or the IMD. The care server 132 may include IMD data, IMD settings, personal, identity or financial information about patients such as a patient social security number, a medical record number, health insurance information, payment information, banking information, credit card information, driver's license information, and state identification information. The care server 132 can be remote from the reader 116 and from the IMD 110, and be in direct or indirect bi-directional communication with the reader 116 and the IMD 110. "Remote" is used to mean not in the same physical space, although it does not require a particular distance of separation.

In one embodiment, the reader 116 can also communicate with an external storage media. The communication with the external storage media allows storage of IMD data and settings of the IMD, as well as other data of the patient. In the embodiment of FIG. 1, the external storage media is a part of a care server 132. It is also possible for the external storage media to be a portable storage device, such as a flash drive or magnetic card. Although the term "server" will be used to describe the storage location in a number of embodiments described herein, including the embodiments of FIG. 1, it will be understood that it is also possible for the same data to be stored on an external storage media different than a server. In one embodiment, the reader includes a local memory location. In addition or alternatively, some information is stored in a local memory location while some information is stored on an external storage media such as a server.

One example of an IMD 110 is a subcutaneous implantable cardiac monitor (ICM). In some examples, ICMs are about one-third the size of a AAA battery and can be inserted using a minimally invasive procedure. The ICM can detect heart rhythms without requiring that leads are positioned in the heart. Another example of an IMD 110 is a cardiac resynchronization therapy (CRT) device which includes leads positioned in the patient's heart. Other examples of IMDs will be described herein.

Transdermal Carrier Wave Options

A transdermal carrier wave is a wave that propagates through body tissue, especially when a skin contact is made. The transdermal carrier wave carries information that can be received by a transdermal carrier wave transceiver. Sending a transdermal carrier wave through body tissues involves physical contact with the patient's body at skin, mouth, another body cavity, or another part of body.

One example of a transdermal carrier wave is an electrical conductive wave. A transceiver for an electrical conductive wave includes at least two electrodes. Electrodes are often present in cardiac and other types of IMDs. A small current is injected into the body using the electrodes. One example of IMD that uses electrical conductive waves is a leadless cardiac pacemaker (LCP), where communication between a subcutaneous implantable cardiac device (SICD) and a leadless cardiac pacemaker (LCP) is used to command the leads to provide pacing.

One other example of a transdermal carrier wave is an acoustic wave, such as an ultrasound wave, a very high frequency audible acoustic wave, or a very low frequency audible acoustic wave. An acoustic transceiver can be included in the IMD and in the reader. An acoustic wave will reflect at the interface of air and skin due to acoustic impedance mismatch. If body contact, such as skin contact, is made with the device-body contact surface, then an air-skin interface and reflection of acoustic waves at an air-skin interface can be avoided. In some embodiments, impedance matching gel can be used at the device-body contact surface to facilitate transmission of the transdermal carrier waves into the body tissue. In some examples, an acoustic transceiver includes a piezoelectric crystal sandwiched between electrodes.

Another example of a transdermal carrier wave is an optical wave, which uses an optical transceiver in the reader and in the IMD. Optical waves travel in straight lines, and will follow a direct line through body tissue. In one embodiment using optical waves, a device body contact surface 118 of a reader is positioned in contact with the patient 112 over the IMD 110 at a fairly close distance from the IMD and with the IMD is just under the skin.

RF Communication Mode

The reader is capable of communicating wirelessly and without body contact with the IMD in an RF communication mode using wireless RF signals. Wherever wireless communication between two components is discussed herein, including but not limited to wireless communication between the IMD and the reader, it should be understood that in some examples the wireless communication is accomplished using a standard for wireless exchange of data over short distances. Further, in some examples, the standard uses short-wavelength ultra-high frequency (UHF) radio waves in the industrial, scientific and medical (ISM) radio band from 2.4-2.485 Gigahertz. In some examples, the standard uses frequency-hopping spread spectrum radio technology, such as BLUETOOTH® communication protocols. Standards for BLUETOOTH® communication are managed by the Bluetooth Special Interest Group. In some examples, a ZIGBEE® communication protocol is used. Standards for ZIGBEE® communication are managed by the Zigbee Alliance.

Figure 3:
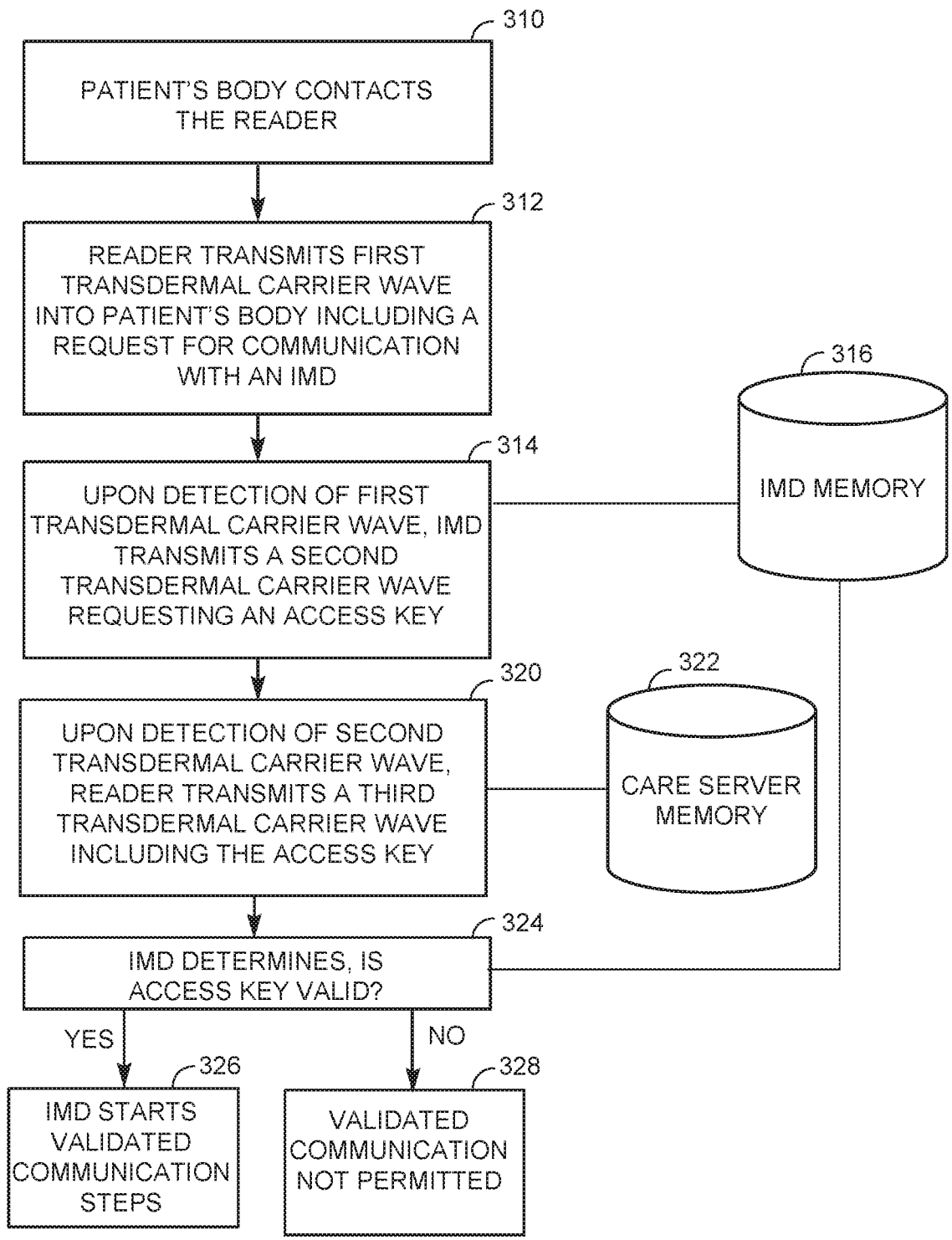
FIG. 3 is a flowchart showing one example of a method of validated communication between an IMD and an external reader using transdermal carrier waves.

Method of Secure Transdermal Communication (FIG. 3)

FIG. 3 is a flowchart showing one example of a method of validated communication between an IMD and an external reader using transdermal carrier waves. In one example, the reader initiates the communication sequence, such as by making an inquiry of the IMD for IMD information, using transdermal carrier waves. To enable that request, in step 310 the patient's body is brought into contact with the reader. In one example, the patient's body, such as the skin, is brought into contact with the device-body contact surface of the reader. In one example, a patient's fingertip having a fingerprint is brought into contact with the device-body contact surface at step 310.

At step 312, the reader transmits a first transdermal carrier wave from the transdermal carrier wave transceiver at the device-body contact surface into the patient's body, wherein the first carrier wave comprises a request for communication with the IMD. The request for communication may also be a request for specific IMD information, an IMD report, or patient information.

At step 314, upon detection of the first carrier wave by the transdermal carrier wave transceiver of the IMD, the IMD responds by asking for an access code from the reader. The request for an access code is transmitted in a second transdermal carrier wave from the IMD into the patient's body.

In some examples, the IMD will access IMD memory 316 to formulate the request for an access code, as will be further described herein.

At step 320, upon detection of the second transdermal carrier wave, the reader determines the access key and transmits a third transdermal carrier wave including the access key. The reader may communicate with a care server memory 322 in the process of determining the access key. At step 324, the IMD determines if the access key is valid.

If the access key is valid, the IMD starts validated communication steps at step 326. Because the access key has been provided, the validated communication is permitted. Examples of validated communication include the IMD transmitting information by radio frequency (RF) in an RF communication mode or the IMD transmitting a fourth transdermal carrier wave including data from the IMD in transdermal communication mode. If the access key is not valid, the IMD will not permit validated communication at step 328.

In some embodiments, passive transdermal carrier waves can be sent from the IMD instead of actively-generated transdermal carrier wave. In these embodiments, the IMD can use energy from a detected transdermal carrier wave to power the transmission of a transdermal carrier wave. In one example, data is passively written into a reflected first transdermal carrier wave to form the second transdermal carrier wave. In one example, energy of the detected transdermal carrier wave from the reader is received and stored in a supercapacitor and that energy is used to send a responsive transdermal carrier wave from the IMD to the reader. For example, energy of the detected first transdermal carrier wave is used by the IMD to send the second transdermal carrier wave.

Access Key Options

There are many options for how the access key is determined by the reader. There are also many options for how the access key can be determined by the IMD before it is requested from the reader. In one example, the access key is stored in a particular address of the IMD memory, and each authentic reader is programmed with the particular address so that reader can obtain and provide the correct access key. In one example, the third transdermal carrier wave from the reader to the IMD can direct the IMD to read the access key from the particular address of the IMD memory. In addition or alternatively, the IMD can provide the reader with the content of the particular address of the IMD memory, and the IMD can use that content to generate the access key. The content of the particular address of the IMD memory may change over time, rotate between a set of options, or stay the same.

In addition or alternatively, the access key is related to a medical record which is stored both in the IMD memory 316 and in the care server memory 322. In order to generate the access key, the reader accesses the medical record on the care server memory 322, then generates the access key and provides it to the IMD in the third transdermal carrier wave. The IMD accesses the corresponding medical record in the IMD memory to generate the access key. The IMD compares the IMD-generated access key with the reader-provided access key. The access key can be a portion of medical record data, or can be a value or code generated using the portion of medical record data as input. In this scenario, hackers attempting to communicate with the IMD inappropriately would have a significant hurdle to surmount in accessing the patient's medical records, identifying the correct piece of data from the medical records, and generating the access code.

Examples of medical records that could be the basis for an access key include physiological waveforms, such as electrocardiogram (EGM) waveforms, for the patient from a specified time period that exists in storage on the IMD and on the care server memory. In one example, a EGM waveform shape occurring at a specified time and on a specified channel of the IMD is the access key. In addition or alternatively, a calculation based on that waveform shape generates the access key. Another example of a medical record that could be the basis for an access key is data in an IMD report, such as data in an episode report, from a particular time. The timeframe for the medical record data could be specified as a date, such as Aug. 3, 2015 at 2 PM. The timeframe could also be specified as a time period before the date or time of the request, such as data in the most current IMD report before the time of the request, or the data at one day, one week, one month or one year before the request.

In one example, the request for an access key is a request for sparsely-sampled, noncontiguous medical data that exists in storage on the IMD and on the care server memory. For example, the access key could be second digit of 20 different values present in an IMD report or the sum or other formula output of that string. In one example, the access key does not include recognizable patient information. As a result, fewer regulations govern the transmission of that data compared to if recognizable patient information forms part of the access key, and there is a reduced risk of unauthorized access to sensitive data.

Figure 4:
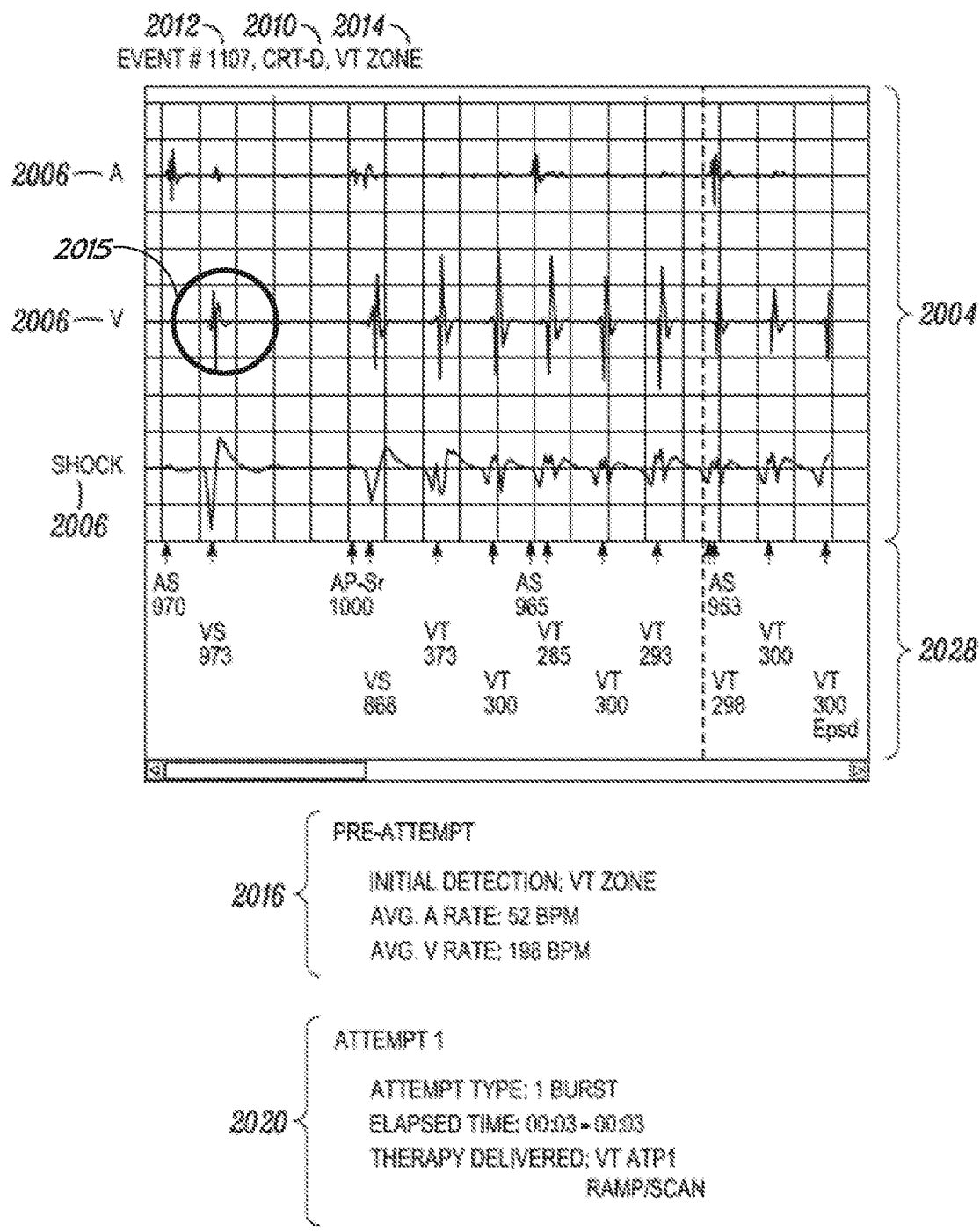
FIG. 4 is an arrhythmia episode report which is one example of a medical record that is used to generate an access key for validated communication in one embodiment.

FIG. 4 is illustrates data in an arrhythmia episode report from an IMD which is one example of a medical record that can be used to generate an access key for validated communication. The report includes an EGM 2004, including labels 2006 indicate which parts of the EGM are sensed in the atrial and ventricular portions of the heart, as well as which parts are for the pacing pulses generated by the device. The report includes the device type 2010, indicating in this example that the device is a cardiac resynchronization therapy defibrillator (CRT-D), the episode number 2012 for identifying the episode within the episode database, and an episode classification 2014, which in this case indicates ventricular tachy arrhythmia (VT). The EGM 2004 includes a circled EGM portion 2015 on the ventricular channel. In one example, the access key is the shape of an EGM portion 2015.

The episode report of FIG. 4 includes device diagnostic information 2016, including average atrial heart rate, average ventricular heart rate, and the zone into which the device has classified the arrhythmia. The episode report of FIG. 4 further includes therapy information 2020 and pace and sense markers 2028 to indicate ventricular sensing (VS), atrial sensing (AS) and the detection of ventricular tachy arrhythmia (VT). Each of the pieces of data in the episode report is an example of medical data that can be used as an access key, as a portion of an access key, or as input into a calculation or derivation to generate an access key. FIG. 4 is one example of how data on an episode report can be displayed to a user. The same data is stored in the IMD memory and in the patient care memory in a format readable by the processors of those devices.

In one example, the reader reads a fingerprint of the patient using the device-body contact surface, take in and generates information about the fingerprint, and generates the access key based on the fingerprint of the patient. For example, the access key could be an image of a portion of the fingerprint, an image of major features of the fingerprint, or code that is generated by performing calculations using information within the fingerprint image. In this example, the reader may not need to communicate with the care server memory 322 to generate the access key. The reader may be programmed with the method for obtaining the access key from the fingerprint. The IMD memory 316 would have the access key stored in memory and would compare it to the access key provided by the reader.

In some examples, the access key allows RF communication for a specified period of time or a specified number of queries, and then a new access key is provided to authorize further RF communication. Examples of the specified period of time or number of queries include 5 minutes, 10 minutes, one hour, five queries, 10 queries or a queries up to a specific data size In one example, the system can facilitate communication with the IMD using a patient safety access key, where a patient safety access key is stored in the memory of each authorized reader. In one example, if the patient safety access key is received by the IMD either by transdermal carrier wave or by RF communication, the IMD will provide basic and limited safety information. Examples of safety information include such as blood type, patient identification, implanted device model, drug allergies, food allergies, emergency contact information, insurance information, medical history, severe conditions, do not resuscitate orders, advanced directives, organ donor information, medical powers of attorney, and other basic or safety information. Obtaining basic or safety information from an IMD can improve patient outcomes and even save lives, especially in the context of an emergency, collapsed patient, or a patient who is unable to communicate.

In one example, special purpose access keys can be stored in the memory of authorized readers to allow communication with the IMD to provide information for a specific limited purpose. Examples of such information include airline flight information, patient ID information, payment information or other types of information to facilitate airport security screening, airline flight check-in, unlocking a lock, providing electronic access, or purchasing goods. In some examples, if the special purpose access key is received by the IMD by transdermal carrier wave, then the IMD will provide the relevant information either by transdermal carrier wave or by RF communication. In some examples, if the special purpose access key is received by the IMD by RF communication, then the IMD will provide the relevant information by RF communication.

The type of access key required by the IMD can vary depending on the risk associated with the type of information or operation that is requested by the reader. For example, if the reader requests only EGM data without sensitive information, a patient safety access key or a preexisting code based on specific memory location in IMD may be sufficient. But if the request is to change the IMD configuration, such as a pacemaker's pacing threshold, a medical record-based key or biometric key may be needed.

A set of temporary access keys may also be used to control access to moderately secure IMD content. During an exchange, the IMD and reader agree upon a set of temporary access keys that will grant a limited number of accesses to the IMD when a reader cannot establish communication with a different type of access key, such as an access key related to a medical record or a memory location of the IMD. For example, if the reader normally communicates with the care server to obtain information from the medical record to generate an access key, but cannot due to lack of internet access, one of the temporary access keys can be used. These keys would expire after a limited number of uses and then require a different access key, such as an access key related to the medical record or an IMD memory location, for access to be granted.

Figure 5:
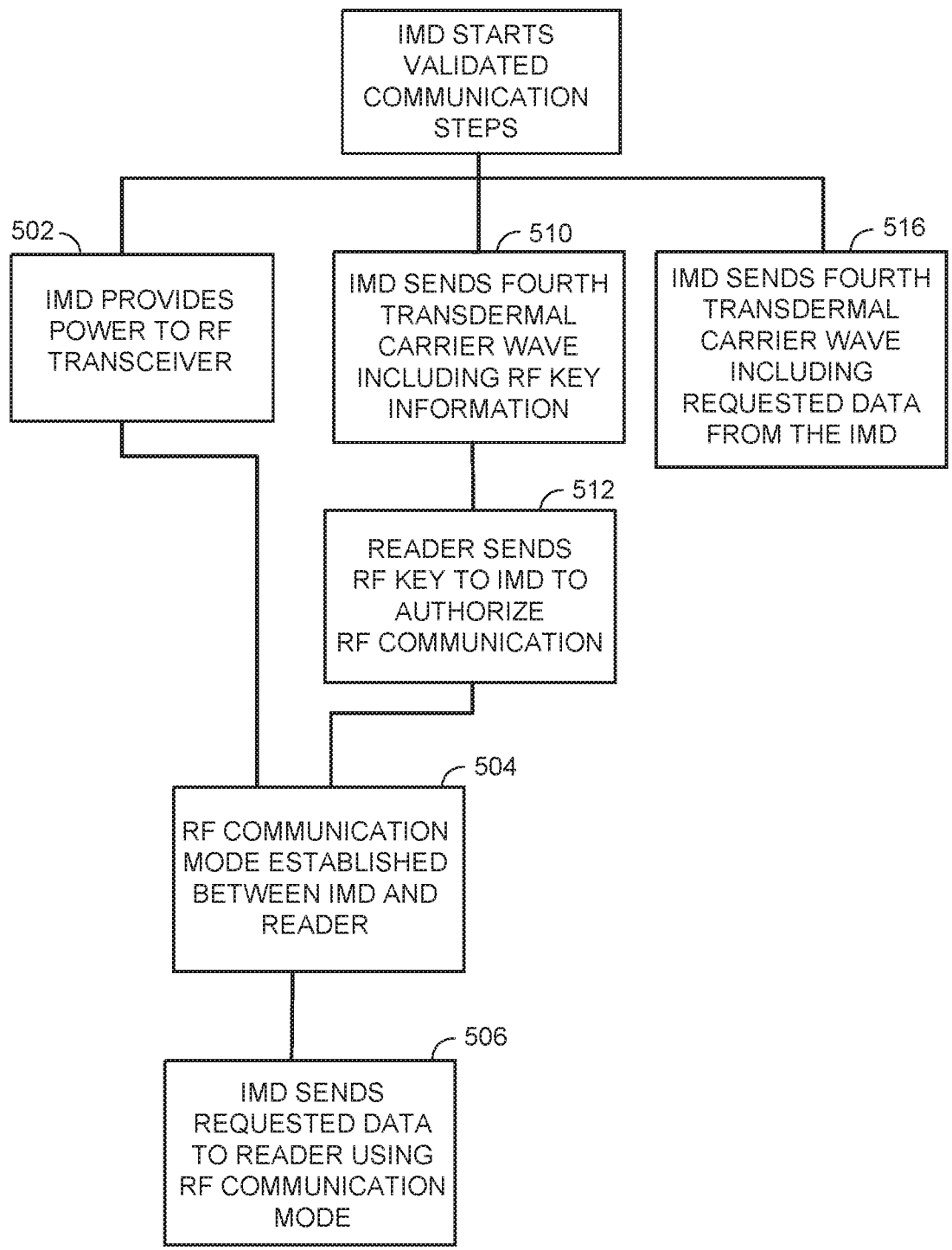
FIG. 5 is a flowchart showing one example of a method for the IMD starting validated communication of data from the IMD.

Data Communication Options after Access Key is Validated Using Transdermal Communication (FIG. 5)

FIG. 5 is a flowchart showing three example methods for the IMD starting validated communication of data from the IMD. In one example, at step 502, if the access key is valid, the IMD provides power to an RF transceiver of the IMD. At step 504, RF communication between the IMD and reader is established and further communication switches to the RF communication mode. Then the IMD can send the requested data to the reader using the RF communication mode at step 506. Data can be transferred more efficiently and at higher data transfer rates by RF communication than by transdermal carrier waves. The RF communication mode, once authorized, can be performed without body-device contact.

In addition or alternatively, if the access key is valid, the IMD transmits an RF key using a fourth transdermal carrier wave at step 510, where the RF key is needed for RF communication with the IMD. The reader uses the RF key to unlock RF communication mode with IMD at step 512. Next, at step 504, RF communication between the IMD and reader is established and further communication switches to the RF communication mode. Then the IMD can send the requested data to the reader using the RF communication mode at step 506.

In addition or alternatively, the IMD can use the highly secure transdermal communication mode for transmitting the IMD data. In this example, if the access key is valid, the IMD sends the IMD data via a fourth transdermal carrier wave at step 516.

The communication used to send IMD data to the reader may depend on the security need presented by the context of the reader's request for communication. For example, if IMD data that does not identify the patient, such as an EGM episode report or EGM snippet, the IMD could start RF communication mode to transfer the data to the reader as in steps 504 and 506, without requiring an RF key to be received by transdermal communication. In addition or alternatively, more sensitive patient information such as a social security number will only be transferred to the reader using the transdermal communication mode of step 516.

Reader Form Factor (FIGS. 1, 2, 6 & 7)

Figure 6:
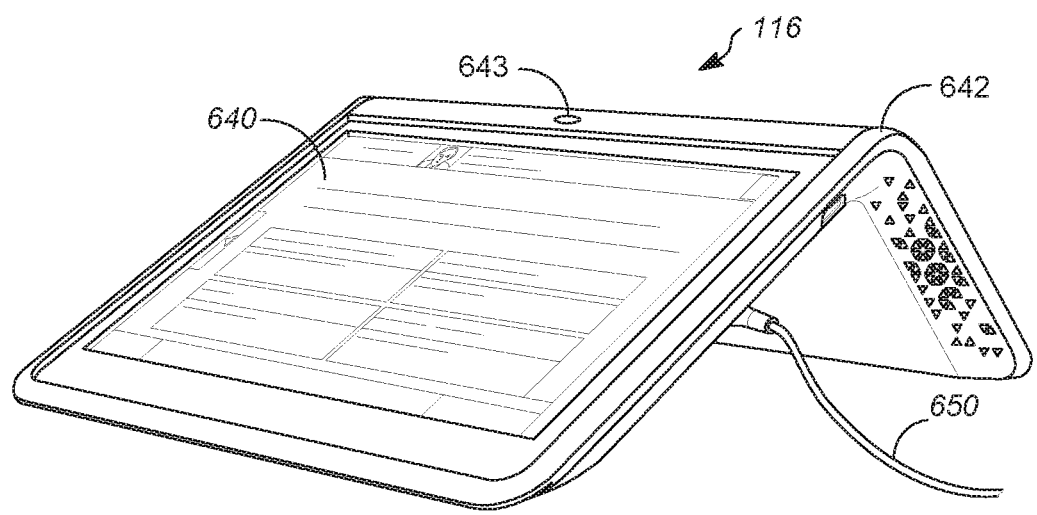
FIGS. 6 & 7 are front and rear perspective views of the reader of FIG. 1.
Figure 7:
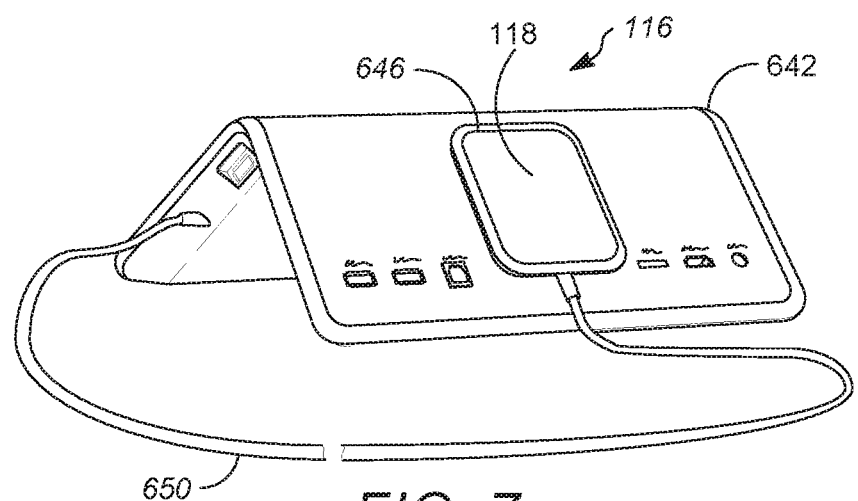

FIGS. 6 and 7 are front and rear perspective views of one example of a form factor of a reader 116 of FIGS. 1 and 2, including a device body contact surface 118, but many other options are possible. Reader 116 is shown as a tablet-style computer. The reader may also take the form of a smart phone. In one example, the transdermal carrier wave transceiver is incorporated into an external surface of a housing of a smart phone. Alternatively, the reader may take the form of a wearable device, a watch-style device, an IMD programmer, a ruggedized laptop computer, a laptop computer, a desktop computer, a tablet computer, or another configuration.

In one embodiment, the reader 116 includes a touch screen 640 and a housing 642. The reader can include a camera 643, one or more speakers, and a microphone. In other embodiments, the reader 116 includes other user input devices such as a keyboard and a mouse. In the patient location setting, a health care professional can use the reader to program IMDs, record data from IMDs, allow monitoring of the implanted device and upload information to a care server 132.

In one example, the device body contact surface 118 can be provided with impedance-matching gel to facilitate transmission of acoustic carrier waves into the patient's body. In one optional embodiment, a portion 646 of the reader 116 encloses the transdermal carrier wave transceiver, is easily attachable and detachable from the housing 642, and is connected to the housing 642 by a flexible cord 650.

In one embodiment, the reader 116 is configured for portability by a user. For example, in one embodiment, the weight of the reader 116 is less than three pounds. In another embodiment, the reader 116 less than two pounds. In one embodiment, a power source of the reader 116 is contained within the housing 642.

Figure 8:
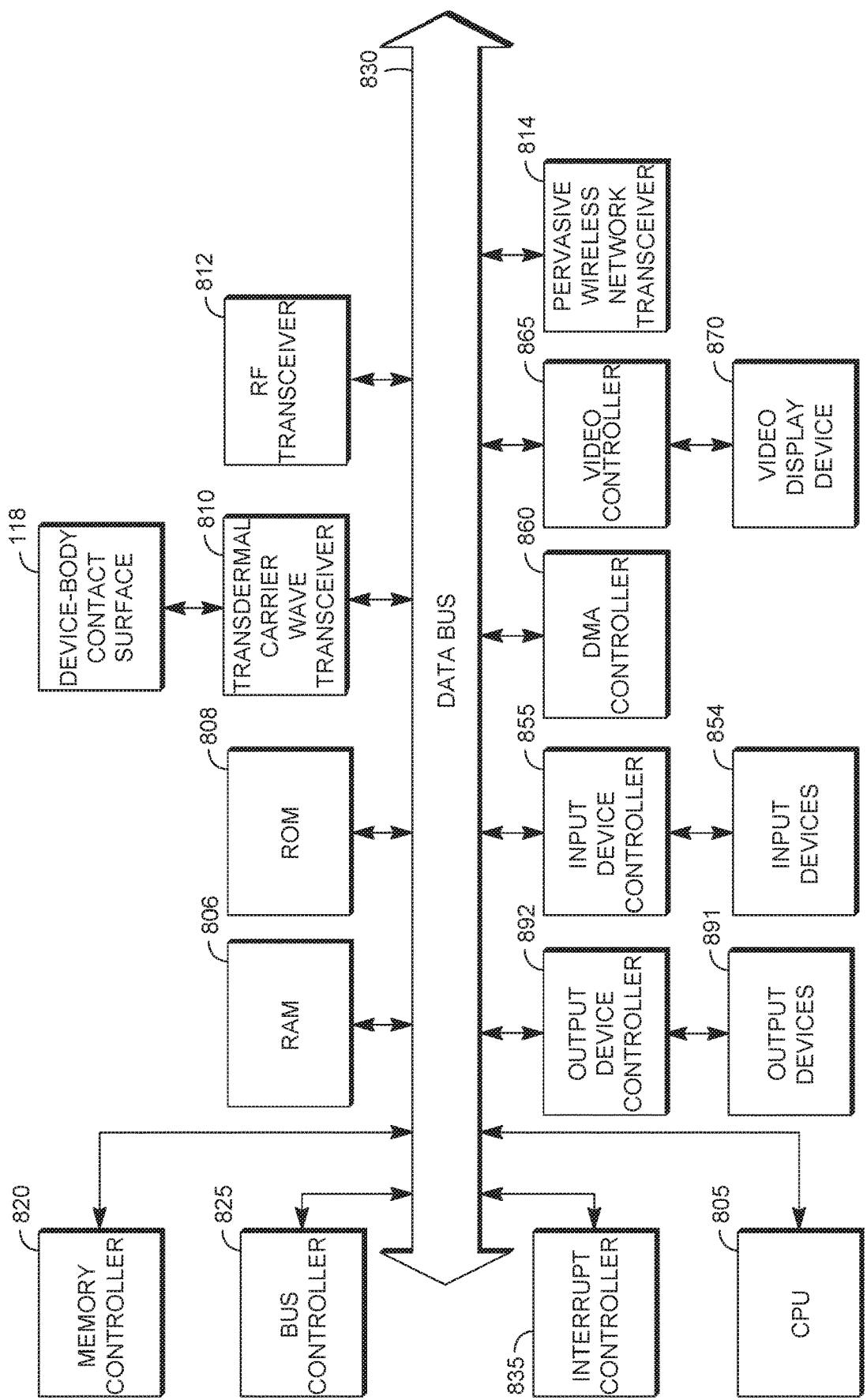
FIG. 8 is a schematic diagram of an implementation of the components of a reader, in accordance with various embodiments.

Options for Reader Hardware (FIG. 8)

FIG. 8 is a schematic diagram of an implementation of the components of a reader, in accordance with various embodiments. The reader can include components common to many computing devices, including smart phones, such as a central processing unit (CPU) 805 or processor, which may include a conventional microprocessor, random access memory (RAM) 806 for temporary storage of information, and read only memory (ROM) 808 for permanent storage of information. RAM 806 and ROM 808 are examples of reader memory.

The reader includes a transdermal carrier wave transceiver 810 in communication with or forming part of the device body contact surface 118. The reader also includes an RF transceiver 812. In some embodiments, the reader includes a pervasive wireless network transceiver 814 for communicating with the care server 132. The reader 118 may include other equipment for interfacing with the care server 132, such as an ethernet cable receptacle.

In some embodiments, a reader is also a programmer of an IMD. As used herein, the term programmer refers to a device that programs IMDs and records data from IMDs. A programmer may also allow monitoring of the implanted device.

A memory controller 820 is provided for controlling system RAM 810. A bus controller 825 is provided for controlling data bus 830, and an interrupt controller 835 is used for receiving and processing various interrupt signals from the other system components.

Mass storage (not shown) can be provided in a variety of ways, such as by a solid state drive, a diskette drive, a CD-ROM drive, a hard disk drive, or other storage options. User input to the interface device system may be provided by a number of devices. For example, input devices 854 such as a keyboard and mouse can connect to bus 830 by input device controller 855. DMA controller 860 is provided for performing direct memory access to system RAM 806. A visual display is generated by a video controller 865 or video output, which controls video display 870. In addition to the visual display, the interface device may include other components for communicating with a user, such as speakers. For example, output devices 891 such as speakers can connect to bus 830 by output device controller 892.

The system can also include a telemetry interface or telemetry circuit which allows the system to interface and exchange data with an implantable medical device. In some examples, the telemetry interface is capable of inductive communication with the IMD, in some cases using an inductive wand. In some embodiments, the reader does not include hardware for inductive communication such as an inductive wand. A pattern recognition analysis module, a seeding module, parameter interaction module, pace timing optimization module and combinations thereof can be present in the interface device in different embodiments.

Implanted Medical Device (IMD)

One example of an IMD 110 is a cardiac IMD, which may include leads and be located near the patient's heart. Examples of IMDs 110 include, without limitation, a cardiac device, a pacemaker, a defibrillator, a cardiac resynchronization therapy (CRT) device, a single chamber implantable cardioverter defibrillator (ICD), a dual chamber ICD, a cardiac resynchronization therapy defibrillator (CRT-D), an implantable cardiac monitor (ICM), a leadless cardiac pacemaker (LCP), a subcutaneous implantable cardiac device (SICD), an insulin pump, a loop recorder, a neuro-stimulator, a physiological sensor, a glucose meter or a combination of such devices.

Figure 9:
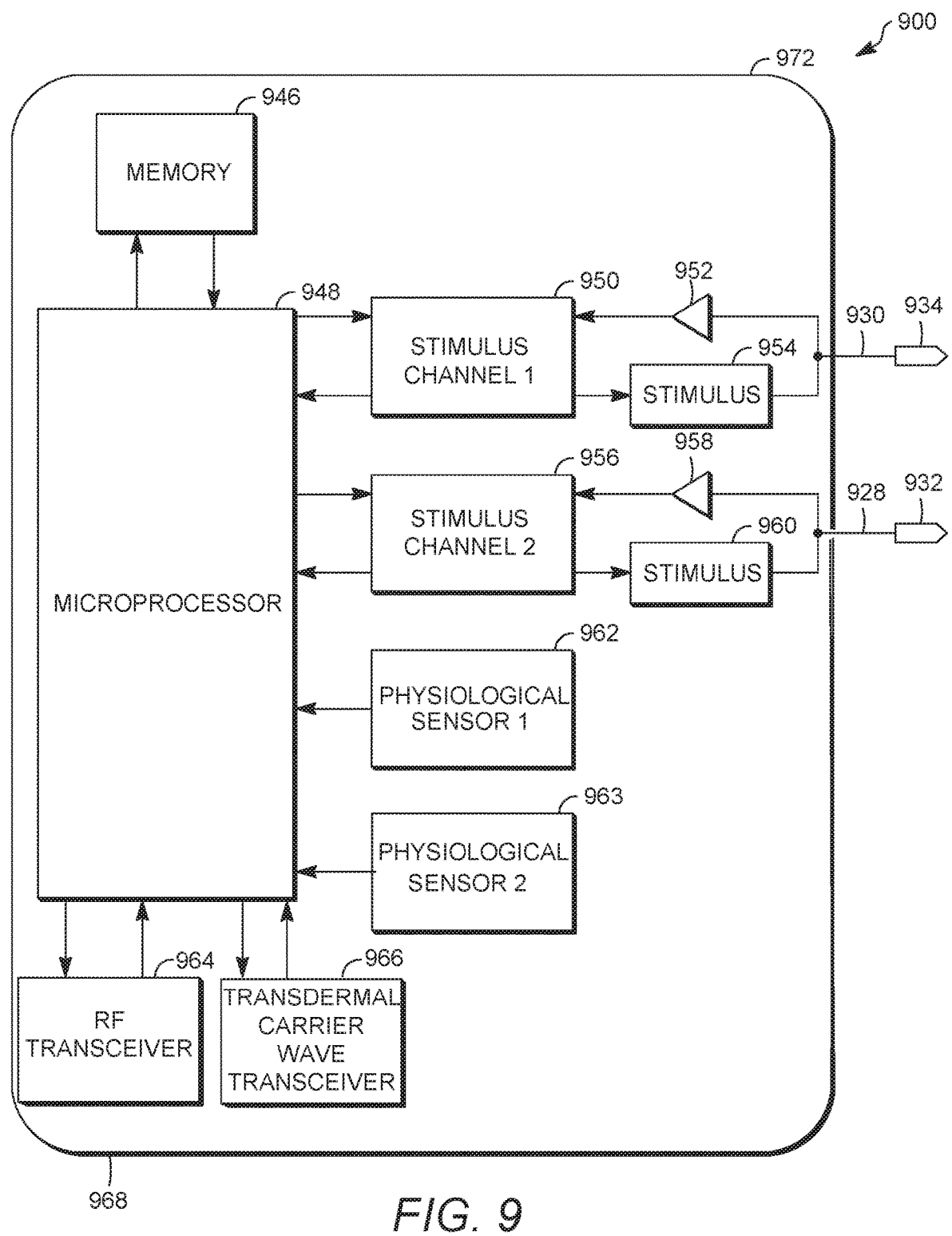
FIG. 9 is a block diagram of one example of an implantable medical device.

Referring now to FIG. 9, some components of an exemplary implantable system 900 are schematically illustrated. The implantable system 900 can include an IMD 972 coupled to one or more stimulation leads 928 and 930. The IMD 972 can also include a first physiological sensor 962, a second physiological sensor 963, and one or more additional sensors. Examples of physiological sensors are electrodes, a pressure sensor, impedance sensor and others. In some examples, the IMD 972 does not include stimulation leads 928 and 930. In some examples, the IMD 972 includes only one physiological sensor.

An RF transceiver 964 is provided for communicating with the reader in an RF communication mode. A transdermal carrier wave transceiver 966 is provided for communicating with the reader in a transdermal communication mode. In some examples, the transdermal carrier wave transceiver 966 is in communication with, takes the form of, or forms part of a housing 968 of the IMD 972.

The IMD can include a microprocessor 948 (or processor) that communicates with a memory 946 via a bidirectional data bus. The memory 946 typically comprises ROM or RAM for program storage and RAM for data storage. The IMD can be configured to execute various operations such as processing of signals and execution of methods as described herein.

The IMD can include first sensing and pacing channels comprising sensing amplifier 952, output circuit 954, and a stimulus channel 1 interface 950 which communicates bi-directionally with a port of microprocessor 948. The first sensing and pacing channel can be in communication with stimulation lead 930 and electrode 934. In one example, the first sensing and pacing channel is a ventricular sensing and pacing channel. The IMD can include second sensing and pacing channels comprising sensing amplifier 958, output circuit 960, and a stimulus channel 2 interface 956 which communicates bi-directionally with a port of microprocessor 948. The atrial sensing and pacing channel can be in communication with stimulation lead 928 and electrode 932. In one example, the second sensing and pacing channel is a atrial sensing and pacing channel. For each channel, the same lead and electrode can be used for both sensing and pacing. The channel interfaces 950 and 956 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

A seeding module, parameter interaction module, pace timing optimization module and combinations thereof can be present in the device in different embodiments.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference in their entirety to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

The invention has been described with reference to various specific and preferred embodiments and techniques. However, it should be understood that many variations and modifications may be made while remaining within the spirit and scope of the invention.

What is claimed is:

1. A method of communication between an implanted medical device (IMD) implanted in a patient and an external reader, comprising:
   bringing a portion of a patient's body into contact with a device-body contact surface of an external reader, wherein an IMD is implanted in the patient;
   the reader transmitting a first transdermal carrier wave from the contact surface into the patient's body, wherein the first carrier wave comprises a request for communication with the IMD;
   upon detection of the first carrier wave, the IMD transmitting a second transdermal carrier wave comprising a request for an access key from the reader, wherein the second transdermal carrier wave includes or is related to an IMD value stored in a memory location of the IMD;
   upon detection of the second transdermal carrier wave, the reader transmitting a third transdermal carrier wave comprising the access key back to the IMD, wherein the access key is based on the IMD value present in the memory location of the IMD;
   the IMD examining the access key for validity; and
   if the access key is valid, the IMD transmitting one of the group of:
     information by radio frequency (RF) in an RF communication mode, and
     a fourth transdermal carrier wave comprising data from the IMD.

2. The method of claim 1 wherein if the access key is valid, the IMD provides power to an RF transceiver of the IMD.

3. The method of claim 1 wherein if the access key is valid, the IMD transmits by RF one of the group consisting of:
   data from the IMD, and
   an RF key needed for further communication with the IMD.

4. The method of claim 1 wherein the first, second, third and fourth transdermal carrier waves are selected from the group comprising electrical conductive waves, optical waves and acoustic waves.

5. The method of claim 1 wherein:
   the IMD value is present in a specific memory location of the IMD.

6. The method of claim 1 wherein:
   the second transdermal carrier wave sent from the IMD includes a first request related to a medical record that is stored on the IMD, and
   the access key sent by the reader in the third transdermal carrier wave is based on the medical record.

7. The method of claim 6 wherein the first request related to the medical record is one of the group consisting of:
   a waveform request for a physiological waveform of the patient from a specified time period that exists in storage on the IMD,
   an EGM request for an electrocardiogram waveform of the patient from a specified time period that exists in storage on the IMD,
   a sample request for sparsely-sampled, noncontiguous medical data that exists in storage on the IMD,
   an episode report request for a portion of an episode report that exists in storage on the IMD, and
   a calculation request for a calculation using as input values of medical record data in storage on the IMD.

8. The method of claim 1 wherein bringing a portion of a patient's body into contact comprises bringing a fingerprint of a patient into contact with the device-body contact surface, further comprising:
   the reader reading a fingerprint of the patient using the device-body contact surface, and
   the reader generating the access key based on the fingerprint of the patient.

9. The method of claim 1 wherein the IMD uses energy from the first transdermal carrier wave to power the transmission of the second transdermal carrier wave.

10. The method of claim 1 wherein the first carrier wave comprises a request for a patient safety communication and a patient-safety access key, wherein patient-safety communication comprises one of the group consisting of the patient's name, the patient's allergies, the patient's blood type and the patient's emergency contact information.

11. A system for communication between an implanted medical device (IMD) implanted in a patient and an external reader, comprising:
   an IMD capable of being implanted into a patient's body, the IMD comprising:
      a transdermal wave transceiver,
      a radio frequency transceiver
   an external reader comprising:
      a device-body contact surface;
      a transdermal wave transceiver capable of transmitting transdermal carrier waves from the contact surface into the patient's body,
      a radio frequency transceiver;
   wherein the reader is operable to transmit a first transdermal carrier wave from the contact surface into the patient's body, wherein the first carrier wave comprises a request for communication with the IMD;
   wherein, upon detection of the first carrier wave, the IMD is operable to transmit a second transdermal carrier wave comprising a request for an access key code from the reader wherein the second transdermal carrier wave includes or is related to an IMD value stored in a memory location of the IMD;
   wherein, upon detection of the second transdermal carrier wave, the reader is operable to transmit a third transdermal carrier wave comprising the access key back to the IMD wherein the access key is based on the IMD value present in the memory location of the IMD;
   wherein the IMD is operable to examine the access key for validity upon receipt from the reader; and
   wherein, if the access key is valid, the IMD is operable to transmit one of the group of:
      information by radio frequency (RF) in an RF communication mode, and
      a fourth transdermal carrier wave comprising data from the IMD.

12. The system of claim 11 wherein if the access key is valid, the IMD is operable to provide power to the RF transceiver of the IMD.

13. The system of claim 11 wherein if the access key is valid, the IMD is operable to transmit by RF one of the group consisting of:
   data from the IMD, and
   an RF key needed for further communication with the IMD.

14. The system of claim 11 wherein the first, second, third and fourth transdermal carrier waves are selected from the group comprising electrical conductive waves, optical waves and acoustic waves.

15. The system of claim 11 wherein:
   the IMD value is present in a specific memory location of the IMD, and
   the access key sent by the reader in the third transdermal carrier wave is based on the IMD value present in the specific memory location of the IMD.

16. The system of claim 11 wherein:
   the second transdermal carrier wave sent from the IMD includes a first request related to a medical record that is stored on the IMD, and
   the access key sent by the reader in the third transdermal carrier wave is based on the medical record.

17. The system of claim 16 wherein the first request related to the medical record is one of the group consisting of:
   a waveform request for a physiological waveform of the patient from a specified time period that exists in storage on the IMD,
   an EGM request for an electrocardiogram waveform of the patient from a specified time period that exists in storage on the IMD,
   a sample request for sparsely-sampled, noncontiguous medical data that exists in storage on the IMD,
   an episode report request for a portion of an episode report that exists in storage on the IMD, and
   a calculation request for a calculation using as input values of medical record data in storage on the IMD.

18. The system of claim 11 wherein the reader is configured to be in communication with a care server, wherein the care server comprises stored medical records for the patient identical to medical records stored on the IMD.

19. The system of claim 11 wherein the IMD comprises an energy harvesting circuit operable to use energy from the first transdermal carrier wave to power the transmission of the second transdermal carrier wave.

20. A method of communication between an implanted medical device (IMD) implanted in a patient and an external reader, comprising:
- bringing a portion of a patient's body into contact with a device-body contact surface of an external reader, wherein an IMD is implanted in the patient;
- the reader transmitting a first transdermal electrical conductive wave from the contact surface into the patient's body, wherein the first transdermal electrical conductive wave comprises a request for communication with the IMD;
- upon detection of the first transdermal electrical conductive wave, the IMD transmitting a second transdermal electrical conductive wave comprising a request for an access key from the reader, wherein the second transdermal carrier wave includes or is related to an IMD value stored in a memory location of the IMD;
- upon detection of the second transdermal electrical conductive wave, the reader transmitting a third transdermal electrical conductive wave comprising the access key back to the IMD wherein the access key is based on the IMD value present in the memory location of the IMD;
- the IMD examining the access key for validity; and
- if the access key is valid, the IMD providing power to a radio frequency (RF) transceiver of the IMD and transmitting IMD data in an RF communication mode.

\* \* \* \* \*